United States Patent
Boschetti et al.

(10) Patent No.: US 7,183,544 B2
(45) Date of Patent: Feb. 27, 2007

(54) BI-FUNCTIONAL POLYMER CHIP

(75) Inventors: Egisto Boschetti, Croissy sur Seine (FR); Luc Bourgeois, Bievres (FR)

(73) Assignee: Ciphergen Biosystems Inc., Fremont, CA (US)

( * ) Notice: Subject to any disclaimer, the term of this patent is extended or adjusted under 35 U.S.C. 154(b) by 0 days.

(21) Appl. No.: 11/014,225

(22) Filed: Dec. 17, 2004

(65) Prior Publication Data

US 2005/0214815 A1 Sep. 29, 2005

Related U.S. Application Data

(60) Provisional application No. 60/533,247, filed on Dec. 31, 2003.

(51) Int. Cl.
*H02J 49/00* (2006.01)
*C12Q 1/68* (2006.01)

(52) U.S. Cl. .......................................... 250/288; 435/6
(58) Field of Classification Search ................. 250/288
See application file for complete search history.

(56) References Cited

U.S. PATENT DOCUMENTS

| | | | |
|---|---|---|---|
| 5,719,060 A | 2/1998 | Hutchens et al. | |
| 6,225,047 B1 * | 5/2001 | Hutchens et al. | 435/5 |
| 6,897,072 B1 | 5/2005 | Rich et al. | |
| 2003/0022216 A1 * | 1/2003 | Mao et al. | 435/6 |

* cited by examiner

*Primary Examiner*—Jack Berman
*Assistant Examiner*—James J. Leybourne
(74) *Attorney, Agent, or Firm*—Foley & Lardner LLP

(57) ABSTRACT

In relation to a chromatographic chip, for protein separation, a polymer surface is provided that has a first polymer layer, attached to a support surface, which can be anionic or cationic. To the first layer is attached a second polymer layer, characterized by an opposite charge.

54 Claims, 1 Drawing Sheet

BI-FUNCTIONAL POLYMER CHIP

BACKGROUND OF THE INVENTION

This application claims the benefit of the priority date of U.S. provisional patent application 60/533,247, filed Dec. 31, 2003.

The present invention relates generally to the field of ion exchange chromatographic materials in the context of separation science and analytical biochemistry.

The increasing need for bulk quantities of biologically relevant molecules (i.e., biomolecules) such as proteins has spawned a variety of techniques for isolating such biomolecules from physiological isolates. Traditional techniques in this regard include precipitation methods, electrophoretic separations, and membrane filtration. One of the more promising separation methodologies advanced, however, is liquid chromatography.

Chromatographic separations of complex biomolecules typically require one or more modifications of the sample that contains the biomolecules. The interactions between biomolecules and a chromatographic sorbent include electrostatic attraction and repulsion, ion exchange, hydrophobic associations, charge transfer, and van der Waals attraction. These forces often compete with each other to impose a delicate balance between conditions that are suitable for a biomolecule to adsorb onto a chromatographic sorbent and those conditions under which the biomolecule may desorb. Difficulties can arise when sorbents are in the presence of highly ionic solutions (such as concentrated sodium chloride) or in the presence of strong acids or bases. It is desirable to have sorbents that can be functionality-modified and still provide an effective sorbent surface, under various ionic and pH condition.

Accordingly, a continued need exists for improved ion exchange-chromatographic materials that exhibit high binding capacity and, in particular, that can be modified to change functionalities, and that are effective under different pH and/or ionic strength conditions.

SUMMARY OF THE INVENTION

To address these and other needs, the present invention provides a biochip comprising (a) substrate comprising a covalently coupled coating that has ionic groups; and (b) polymer coating comprising (1) ionic groups of a charge opposite to the coating, wherein the polymer coating is ionically bound to the substrate coating, and (2) binding groups or EAM functionalities, wherein the biochip is adapted to engage a probe interface of a mass spectrometer. In one embodiment, the substrate coating may comprises anionic groups and the polymer coating comprises cationic groups. Alternatively the substrate coating my comprise cationic groups and the polymer coating comprises anionic groups.

The polymer coating may comprises linear or branched soluble polymer or energy absorbing moieties. The polymer coating can be a natural ionic polymer, a polysaccharide, a polysaccharide derivative, dextran or synthetic ionic polymer. The substrate can be a material selected from metal and synthetic polymer. Other embodiments of the polymer coating include DEAE dextran, a natural polymer, polyethyleneimine, a synthetic polymer, a carboxymethyl dextran polymer, an alginic acid polymer, a polyacrylic acid, anionic groups, hydrophobic groups.

Preferably, the functionality of the binding groups is other than that of the ionic groups of the polymer coating.

Examples of a binding group of the polymer coating is a functionality selected from an anionic functionality, a cationic functionality, a metal chelate functionality, a hydrophbobic functionality, a hydrophilic functionality, a dye functionality or a biospecific functionality. The polymer coating can comprise cationic groups and hydrophobic groups. Preferably, the polymer coating is attached to the substrate coating via ion exchange by a multipoint interaction mode.

Another embodiment of the present invention is a biochip comprising a substrate that is adapted to engage a probe interface of a mass spectrometer, wherein the substrate has a covalently coupled coating that has ionic groups; and a receptacle containing a linear polymer that comprises ionic groups of opposite charge to those on the substrate and binding groups. The invention also encompasses a method of making a biochip, comprising providing a substrate that is comprised of a coating layer of ionic material, bound to the substrate; and contacting the substrate with a linear polymer comprising ionic groups of a charge opposite to those of the ionic material. As a result, the linear polymer attaches to the substrate through ionic bonds.

In another aspect, the invention provides a method for detecting an analyte comprising: (a) providing a biochip of this invention; (b) depositing an analyte on the polymer coating; (c) desorbing/ionizing the analyte from the biochip with photo-irradiation; and (d) detecting the desorbed/ionized analyte. In certain embodiments, the photo-irradiation is laser irradiation, e.g., UV or IR. In certain embodiments, the analyte is associated with an energy absorbing moiety, either through attachment of the EAM functionality to the polymer coating, or application of a matrix material. This detection method is typically used in laser desorption mass spectrometry.

DETAILED DESCRIPTION OF THE PREFERRED EMBODIMENTS

Biochips

Figure 1:
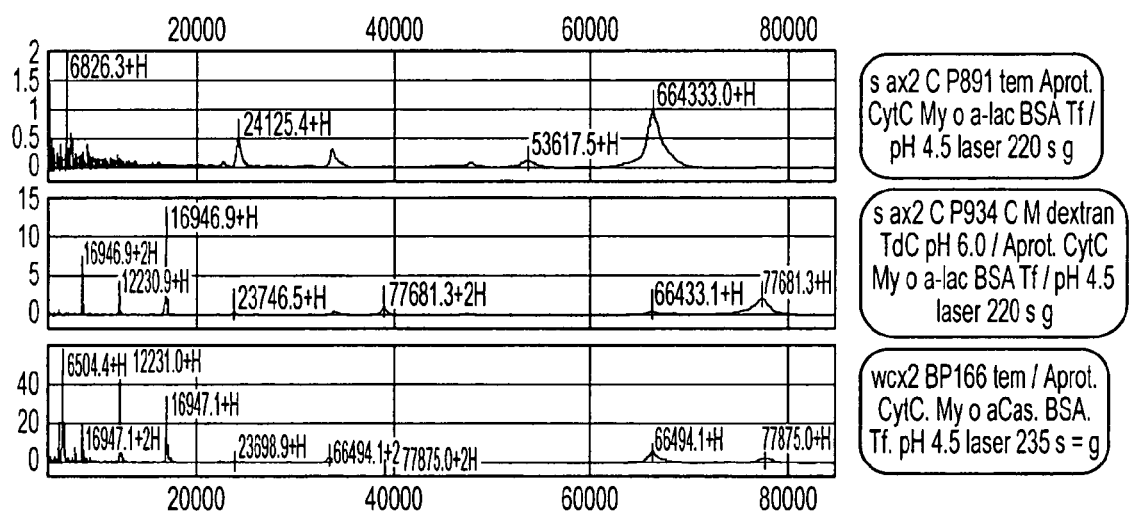
FIG. 1. Mass spectrometry results on surface resulting from the association of SAX chip with carboxymethyl-dextran. Chromatograms of an experiment done at pH 6.0 using standard conditions. From top to bottom the chromatograms are of SAX-2, SAX-2 and CM-dextran, and WCX-2. Proteins were as follows: aprotinin (6504.4+H for WCX-2), cytochrome c (12231.0+H for WCX-2 and 12230.9+H for SAX-2/dextran), myoglobin (16947.1+H for WCX-2 and 16946.9+H for SAX-2), serum albumin (66494.1+H for WCX-2, 66433.1+H for SAX-2/dextran and 66433.0+H for dextran), and transferrin (77875.0+H for WCX-2 and 77681.3+H for SAX-2/dextran).

The present invention relates to the preparation of a polymer surface on a biochip that is suitable for mass spectrometry. A polymer is chosen as a complementary function of the surface functionality of a biochip and is layered upon the biochip. It then is tightly adsorbed on the surface. The polymer also carries chemical functionalities that are appropriate for protein interaction, prior to mass spectrometry. One advantage of the biochip described herein is that the end user can prepare the chip surfaces, by modification of existing chips. The functionality of the chip surface can be changed, easily and rapidly, by the multi-layering of polymers. "Chip" refers to a solid support having a generally planar surface to which a chemical moiety may be attached. A chip that is adapted to engage a probe interface is also called "probe."

"Biochip" refers to a chip to which a chemical moiety is attached. Frequently, the surface of the biochip comprises a plurality of addressable locations, each of which location has the chemical moiety attached there.

A biochip comprises a solid support substrate coated with (e.g., covalently coupled to) a coating that has ionic groups. A polymer having ionic groups is attached to the coating by oppositely charged ionic groups. The polymer also has binding groups having a functionality other than the ionic groups of opposite charge to the coating. These binding groups are for the capture of the analyte. These binding groups for the analyte have a different functionality than the ionic groups that bind the polymer coating to the substrate coating. The different functionalities can give rise to a range of intermolecular forces, such that the chromatographic material provides complementary modes of attracting substances selectively. The biochip is adapted to engage the probe interface of a mass spectrometer. These aspects of the present invention will be discussed in more detail below.

A preferred embodiment has the chromatographic material, thus described, in a "biochip" or microarray format, where the material presents a generally planar surface to which is covalently attached a coating. Thus, a biochip presents a defined region or site—more typically, a collection of defined regions or sites—on which analytes may be captured selectively. Upon capture, analytes can be detected and, optionally, characterized by a variety of techniques, described in more detail below.

Substrate

This invention contemplates a substrate to which the coating is attached. The solid support takes the form of a chip, that is, a solid support having a generally planar surface to which the coating can be covalently attached.

Accordingly, the substrate can comprise a metal, such as gold, aluminum, iron, titanium, chromium, platinum, copper and their respective alloys. Such metals can be derivatized on their surfaces with silicon dioxide, for instance, to provide reactive groups for linking. One method of derivatizing a metal surface is to sputter a metal oxide, such as silicon oxide, onto the metal surface. Alternatively, the solid support can comprise silicon, glass or an organic polymer, such as a plastic. In certain embodiments, the solid support can be transparent.

Coating of the Substrate

The substrate is coated with a layer that has ionic groups, e.g., positively or negatively charged groups. The ionic groups can be selected from any of the well known ionic groups, for example, ammonium groups or carboxyl groups. In the completed chip, these groups will engage in ionic bonding with oppositely charged groups of the polymer coating. The coating need not cover the entire surface of the substrate, but can be localized to addressable locations on the surface.

One method of introducing the coating onto the substrate is by derivatizing the substrate with bi-functional linking molecules. Silane chemistry is particularly useful for this purpose. In one embodiment, a substrate of aluminum or another metal is coated first with silicon dioxide, to provide hydroxyl groups for chemical reaction. The surface then is exposed to a functionalized silanizing reagent, such as a functionalized alkyl alkoxysilane (e.g., amino propyl-trimethoxysilane or -triethoxysilane). The reaction of the alkyloxy groups with the hydroxyl groups on the surface results in a covalent bond by which the silane is attached to the substrate surface. The functional group, such as the amino group or a carboxyl group, can be ionized by exposure to the proper chemical conditions, for example, by raising or lowering pH.

The substrate can be provided with a silane coat, a hydrocarbon silane coat, a fluorinated silane coat, or a mixed fluorinated/hydrocarbon silane coat, inter alia. When oxide substrates are used, alkoxysilane and chlorosilane chemistries can be employed to form the silane coat.

When a substrate is a noble metal, such as gold or silver, then alkanethiols or disulfides can be used to coat the substrate. In addition, the substrate layer can be modified physically. Illustrative of such physical modification include conditioning in order to make the surface rough, porous, or microporous.

The thickness of the substrate coat is not particularly limited but can be, for example, about 4 angstroms to about 10 microns, and more particularly, about 5 nm to about 10 microns. More particularly, a thickness in the range of about 10 nm to about 10 microns is preferred.

In certain embodiments, the ionic coating that forms the surface layer comprises a polymer made from, for example, one or more of 2-arcylamidoglycolic acid), 3-mercaptopropionate, acrylic acid, 3-mercatopropanesulfonate, N-methylglucamine, N,N-dimethyl ethanolamine, methylacrlamido-propyl-trimethyl ammonium chloride, and N-(3-N,N-dimethylaminopropyl)methacrylamide. Via attachment chemistries described above, these monomers of the precoating also can be attached to the surface of the chip. For example, the methacryl silane chemistry could provide a vinyl group for such attachment, upon polymerization.

Polymer Coatings

In the manufacture of a biochip, pursuant to the present invention, polymers that have ionic properties ("ionic polymers") are applied to a biochip surface that carries an oppositely charged, ionic coating. By this approach, the ionic polymer applied to the biochip surface is held in place there by interaction with the ionic coating of the opposite charge. The ionic polymers can be added to the biochip when they are in an ionic solution, by application of the ionic solution to the chip. Preferred ionic polymers comprise acrylamide or dextran coatings, selected for their charge that is opposite to the ionic coating, itself covalently coupled to the substrate. It is preferred that the ionic polymer be linear. Dextran ionizable material can be replaced by other ionizable polymers, natural and/or synthetic.

Instead of starting from already coated surfaces, moreover, it is possible to use a "naked" (uncoated) surface and to select polymers that have an affinity for that surface. The naked surface can be a plastic surface, for hydrophobic or amphiphilic coating polymers. Another example is a gold surface, which has an affinity for thio- or mercury-containing polymers.

The polymer coating should have a molecular weight between 10 K and 1 M Daltons, preferably 100 K to 500 K. The polymer also can comprise energy-absorbing moieties that absorb laser light and contribute to desorption and ionization of intact analyte molecules.

Binding Group Functionalities

The polymers of the polymer coating are further functionalized with binding groups. Generally, the polymers will be functionalized before application to the chip. However, this invention also contemplates functionalization after attachment of the polymers to the chip. The binding group functionality of can be selected according to the properties of the substance for which separation is desired. Examples of binding functionalities are described below.

The binding group can be a hydrophilic group, which is polar chemical entities that is attracted to water or another hydrophilic entity. Hydrophilic entities include hydroxyl.

The term "hydrophobic," as used herein, generally refers to a non-polar chemical moiety that is understood in the art to repel polar entities such as water, or equally, to attract other hydrophobic entities. Exemplary hydrophobic groups contemplated for this invention include but are not limited to alkyl, aryl, alkaryl alkyl groups. Other groups contemplated include ($CH_3(CH_2)_{17}OH$, 1-octadecanol, 1-docosanol, and perfluorinated polyethyleneglycol (Solvay, USA)) groups.

"Alkyl" here refers to a straight or branched or cyclic hydrocarbon having 1 to 16 carbon atoms, preferably 1 to 8 carbon atoms. Exemplary alkyl groups are methyl, ethyl, propyl, butyl, pentyl, and hexyl. An alkyl fragment that is part of a chain is necessarily divalent and is art-recognized as an "alkylene" group.

"Aryl" denotes a cyclic, fused or non-fused, fully aromatic hydrocarbon that has 6 to 12 carbon atoms. Exemplary aryl groups include but are not limited to phenyl, naphthyl, and biphenyl.

Thus, "alkaryl" refers to an alkyl group that is substituted by an aryl group, as each are defined above. Illustrative of the category of alkaryl groups are benzyl and phenethyl.

The functional groups can be anion exchange moieties such as ammonium ions, for example, 3-chloro-2-hydroxypropyl trimethylammonium chloride, 2-hydroethyl-N-methyl pyridium chloride) and polyethyleneimine.

Other functional groups can be cation exchange moieties, such as sulfates, sulphonates, phosphates and carboxylates, for example, 1,4-butanediol-2-sulfonic acid, 3,5-dimethylo benzenesulfonic acid, dihydroxybenzoic acid and dimethylolacetic acid.

Other functional groups include metal ion complexing agents or metal chelators. Examples of metal chelators include N-hydroxyethylethylenediaminoetriacetic acid (NTA), N,N-bis(carboxymethyl)-L-lysine, iminodiacetic acid, aminohydroxamic acid, salicylaldehyde, 8-hydroxyquinoline, N,N,N'-tris(carboxytrimethyl)ethanolamine, and N-(2-pyridylmethyl) aminoacetate. The metal ion complexing agents can complex any useful divalent metal ion, e.g., copper, iron, nickel, cobalt, gallium or zinc.

Other functionalities useful in the present invention are reactive functionalities such as epoxide and carboimidizole. In addition, dye functionalities can be used as the binding group.

EAM Functionalities

In another embodiment, the polymers of the polymer coating are further functionalized with EAM functionalities. EAM (energy absorbing molecule) functionalities are useful for promoting desorption and ionization of an analyte into the gas phase during laser desorption/ionization processes. The EAM monomer comprises a photo-reactive moiety as a functional group. The photo-reactive moiety preferably includes a nucleus or prosthetic group that specifically absorbs photo-radiation from a laser source. The photo-reactive groups absorbs energy from a high fluence source to generate thermal energy, and transfers the thermal energy to promote desorption and ionization of an analyte in operative contact with the polyurethane. In the case of UV laser desorption, the EAM monomer preferably includes an aryl nucleus that electronically absorbs UV photo-irradiation. In the case of IR laser desorption, the EAM monomer preferably includes an aryl nucleus or prosthetic group which preferably absorbs the IR radiation through direct vibrational resonance or in slight off-resonance fashion. A UV photo-reactive moiety can be selected from benzoic acid (e.g., 2,5 di-hydroxybenzoic acid), cinnamic acid (e.g., α-cyano-4-hydroxycinnamic acid), acetophenone, quinone, vanillic acid, caffeic acid, nicotinic acid, sinapinic acid pyridine, ferrulic acid, 3-amino-quinoline and derivatives thereof. An IR photo-reacitve moiety can be selected from benzoic acid (e.g., 2,5 di-hydroxybenzoic acid), cinnamic acid (e.g., α-cyano-4-hydroxycinnamic acid), acetophenone acid (e.g. 2,4,6-trihyroxyacetophenone and 2,6-dihyroxyacetophenone) caffeic acid, ferrulic acid, sinapinic acid 3-amino-quinoline and derivatives thereof.

Addressable Locations

Notably, the arrangement of sites on the surface of a biochip of the invention preferably permits interrogation of multiple sites at the same time, to achieve higher throughput and speed. The use of a biochip is therefore essentially equivalent to concurrently conducting multiple chromatographic experiments, each with a different chromatographic column, but the present biochip has the advantage of requiring only a single system.

It is preferable that an inventive biochip comprise a plurality of addressable locations, and to each such location is tethered a unique combination of hydrophobic linker and terminal binding functionality. The biochip can incorporate a single addressable location or as many as 10, 100, 1000, 10,000 or more addressable locations, which need only be as large as an impinging energy source, such as a laser. In this regard, "addressable" connotes a position on the solid substrate that can be located, e.g., by an energy source, using an appropriate addressing scheme or algorithm. Thus, each addressable location or subsets of locations can bind a biological substance preferentially, and the binding can be located by virtue of the fact that capture occurs at a defined location on the biochip.

The addressable locations can be arranged in any pattern but preferably appear in regular patterns, such as lines or orthogonal arrays, or even as curves, such as circles. Circular arrangements of the addressable locations are particularly useful on disk-shaped biochips. Arranged in this fashion, the addressable locations can provide known gradients of binding capacity on the solid substrate.

Process for Making the Chromatographic Material

The substrate is first prepared by chemically coupling the coating of the substrate so that covalent bonds are formed between the substrate and the coating. In typical scenarios, the solid support is first treated with a bifunctional reagent which serves to introduce onto the solid support reactive groups that form part or all of the hydrophobic linker. For some solid supports, such as cellulose, composites containing a hydrogel, or other materials presenting hydroxyl groups, it is often advantageous to deprotonate the hydroxyl groups with a hydroxide source, for example, prior to reaction with a bifunctional reagent. The bifunctional reagent is capable of reacting both with the solid support and with reagents that contain the terminal binding functionality. Illustrative bifunctional reagents, which contain the same or different functional groups, include but are not limited to epichlorhydrin, epibromhydrin, dibromo- and dichloropropanol, dibromobutane, ethylene glycol diglycidylether, butanediol diglycidylether, divinyl sulfone, allylglycidylether, and allyl bromide. In another scenario the solid support reacts directly with a reactive coating material.

Once functionalized, the solid support is then washed extensively with one or more solvents to remove unreacted bifunctional reagent, reaction byproducts, or both. A typical solvent used in this regard is water.

The polymer coating is introduced to the coating of the substrate by way of reagents that contain such functionalities. Such reagents react with the functional groups that are presented by the functionalized solid support as described above.

The particular pairing of a bifunctional reagent with a binding functionality polymer reagent is guided by well-known chemistries, in which the polymers are adsorbed to the chip by multipoint (i.e. ionic) interaction. In order for the polymers to be adsorbed by a multipoint interaction mode, polymers having an opposite charge to the ionic groups of the coating polymer of the surface of the biochip are chosen.

Methods of Using the Chromatographic Material

In preferred embodiments, the chromatographic material of the present invention can be used to separate and isolate a variety of substances, including biologically relevant molecules such as proteins, viruses, nucleic acids, carbohydrates, and lipids. Other substances that are suitable for separation include oligo- and polysaccharides, pigments, lipopolysaccharides, polypeptides, synthetic soluble polymers and immunoglobins. The biological substances typically derive from, or are contained in, sources including but not limited to liquid samples such as saliva, blood, urine, lymphatic fluid, prostatic fluid, seminal fluid, milk, milk whey, organ extracts, plant extracts, cell extract, cell culture media, fermentation broths, serum, ascites fluid, and transgenic plant and animal extracts.

The "immunoglobulins" category embraces whole immunoglobulins, including monoclonal and polyclonal antibodies, as well as Fab, $F(ab')_2$, $F_c$ and $F_v$ fragments thereof.

Method of Detecting an Analyte

This invention provides a convenient method of detecting an analyte. An addressable location of the biochip as described above is contacted with a sample that contains at least one analyte. The analyte can be a biological substance, such as those described herein, which adsorbs to (i.e., is captured at) the addressable location. The present method thus accommodates the detection of a plurality of analytes contained in a single sample, each analyte being bound to a unique location on the biochip.

The biochip is then preferably washed with an eluant as described above to remove unbound materials. In this context, the introduction of eluant to small diameter spots of the solid substrate is best accomplished by a microfluidics process.

Upon capture on a biochip, analytes can be detected by a variety of detection methods selected from, for example, a gas phase ion spectrometry method, an optical method, an electrochemical method, atomic force microscopy and a radio frequency method. Gas phase ion spectrometry methods are described herein. Of particular interest is the use of mass spectrometry and, in particular, laser desorption mass spectrometry, more specifically, SELDI. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method (e.g., wavelength-interrogated optical sensor) or interferometry). Optical methods include microscopy (both confocal and non-confocal), imaging methods and non-imaging methods. Immunoassays in various formats (e.g., ELISA) are popular methods for detection of analytes captured on a solid phase. Electrochemical methods include voltametry and amperometry methods. Radio frequency methods include multipolar resonance spectroscopy.

Detection of analytes that remain bound to the biochip can be accomplished by a variety of methods. These include microscopy and other optical techniques, mass spectrometry, and electrical techniques. Light-based detection parameters include, for example, absorbance, reflectance, transmittance, birefringence, refractive index, and diffraction measurement techniques.

Fluorescence detection of labeled analytes is particularly popular. Methods involving fluorescence include direct and indirect fluorescent measurement. Specific methods include, for example, fluorescent tagging in immunological methods such as ELISA or sandwich assay.

Other useful techniques include, for example, surface plasmon resonance, ellipsometry, resonant mirror techniques, grating coupled waveguide techniques, multipolar resonance spectroscopy, impedimetric detection, chemiluminescence detection, and electrical conductivity/reduction—oxidation methods. Methods of desorbing and/or ionizing analytes from biochips for direct analysis are well known in the art, and are generally described, for example, in U.S. Pat. No. 6,225,047.

A particularly preferred method of analysis is laser desorption mass spectrometry and, in particular, Surface-Enhanced Laser Desorption/Ionization ("SELDI"), which is described in, for example, U.S. Pat. Nos. 5,719,060 and 6,255,047. In laser desorption mass spectrometry, the analyte is placed on the surface of a probe, typically in association with an energy absorbing molecule or a matrix material. In MALDI, the anayte is mixed with the matrix and then applied to the probe surface. In SELDI, the analyte is captured by the binding groups on the probe surface and then the matrix is applied. Matrix materials are well known in the art and include, for example, sinapinnic acid and CHCA. Alternatively, if the surface has EAM moieties attached, these replace the matrix. In SELDI, an addressable location on the biochip is presented to an energy source such as a laser, which desorbs and ionizes the analyte bound at the addressable location. The ionized analyte is then detected directly in a time-of-flight ("TOF") mass spectrometer, for example, thereby yielding the mass-to-charge ratio of the desorbed analyte. By repeatedly shifting and positioning the biochip within the probe interface to align with the laser, each addressable location on the biochip can be similarly analyzed.

Additionally, an ion mobility spectrometer can be used to analyze samples. The principle of ion mobility spectrometry is based on different mobility of ions. Specifically, ions of a sample produced by ionization move at different rates, due to their difference in, e.g., mass, charge, or shape, through a tube under the influence of an electric field. The ions, which are typically in the form of a current, are registered at the detector which can then be used to identify the sample. One advantage of ion mobility spectrometry is that it can operate at atmospheric pressure.

Furthermore, a total ion current measuring device can be used to analyze samples. This device can be used when the probe has a surface chemistry that allows only a single class of analytes to be bound. When a single class of analytes is bound on the probe, the total current generated from the ionized analyte reflects the nature of the analyte. The total ion current from the analyte can then be compared to stored total ion current of known compounds. Therefore, the identity of the analyte bound on the probe can be determined.

An advantage of the biochips and analytical method of this invention is that binding and detecting analytes are effective in picomolar or even attomolar amounts of analyte. In accordance with the teachings of this invention, it is thus possible to discover certain subclasses of biological substances referred to as biomarkers. In the present context, a biomarker is an organic biological substance, particularly a polypeptide or protein, which is differentially present in a sample taken from a diseased subject as compared to a sample taken from a healthy subject. A biomarker is differentially present in samples taken from diseased subjects if it is present at an elevated level or a decreased level relative to the level present in a sample taken from a healthy subject. The chromatographic material of the present invention, particularly in the form of a biochip, allows the rapid discovery and identification of biomarkers.

This method is useful for protein profiling, in which proteins in a sample are captured using one or more different solid substrates of this invention and then the captured analytes are detected. In turn, protein profiling is useful for difference mapping, in which the protein profiles of different samples are compared to detect differences in protein expression between the samples.

Probes

In a particularly preferred embodiment, the present chromatographic material, in the form of a biochip, is a probe for use in a detection instrument, such as a mass spectrometer. This provides a powerful analytic tool for the capture and identification of known and unknown biological analytes. Illustrative probes are described in U.S. Pat. No. 6,225,047, which is incorporated herein by reference. For example, a mass spectrometer probe ("MS probe") refers to a device that, when positionally engaged in an interrogatable relationship to an ionization source, e.g., a laser desorption/ionization source, and in concurrent communication at atmospheric or subatmospheric pressure with the detector of the preferred Laser Desorption/Ionization Time-Of-Flight spectrometer, can be used to introduce ions derived from an analyte into the spectrometer. Preferred laser sources include nitrogen lasers, Nd-Yag lasers and other pulsed laser sources. Thus, a MS probe typically is reversibly engageable (e.g., removably insertable) with a probe interface that positions the MS probe in an interrogatable relationship with the ionization source and in communication with the detector.

Upon capture on a biochip, analytes can be detected by a variety of detection methods selected from, for example, a gas phase ion spectrometry method, an optical method, an electrochemical method, atomic force microscopy and a radio frequency method. Gas phase ion spectrometry methods are described herein. Of particular interest is the use of mass spectrometry and, in particular, SELDI. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method (e.g., wavelength-interrogated optical sensor) or interferometry). Optical methods include microscopy (both confocal and non-confocal), imaging methods and non-imaging methods. Immunoassays in various formats (e.g., ELISA) are popular methods for detection of analytes captured on a solid phase. Electrochemical methods include voltametry and amperometry methods. Radio frequency methods include multipolar resonance spectroscopy.

The following examples are given to illustrate the present invention. It should be understood, however, that the invention is not to be limited to the specific conditions or details described in these examples. All references to publicly available documents, including patents, are incorporated herein by reference as if set forth fully in their entireties.

EXAMPLE 1

Layering a Polyanionic Saccharide Over a Polycationic Surface

10% solution of carboxymethyl-dextran is first prepared by solubilizing the sodium salt of CM-dextran in water at room temperature. CM-dextran contains in average a carboxyl group every three repeating glucose units. The solution is cleared by filtration and is then layered on the surface of chip spots. The volume of the deposit can vary from 0.5 to 5μ liters. The water is then evaporated and the chip surface extensively washed with water and dried. The carboxymethyl dextran is strongly adsorbed by ion exchange by a multipoint interaction mode. The anionic chip is then used to make MS analysis of protein mixtures.

EXAMPLE 2

Layering a Polyanionic Saccharide Over a Polycationic Surface

The procedure of Example 1 is followed but instead of carboxymethyl-dextran, alginic acid is used as carboxylated polysaccharide. A very similar result to Example 1 is obtained.

EXAMPLE 3

Layering a Polycationic Saccharide Over a Polyanionic Surface

A WCX chip, a polycarboxylic anionic surface, is layered with DEAE dextran to thus obtain a cationic surface. To this end a 5% aqueous solution of DEAE dextran is first prepared. Once the solution is perfectly clear and filtered, it is layered on the surface of chip spots. The volume of the deposit can vary from 0.5 to 5μ liters. The water is then evaporated and the chip surface extensively washed with water and dried. The DEAE dextran is attached by ion exchange by a multipoint interaction mode. The cationic chip then is used classically to make MS analysis of protein mixtures.

EXAMPLE 4

Double Layer Anionic Surface

In a third approach, the chip surface obtained after deposit of DEAE dextran as described on example 3 is used for the preparation of an anionic surface using carboxymethyl-dextran as described on example 1 above. In this case a double layer of dextran is obtained with a net negative charge. The functionality of the chip is fully anionic, therefore. The resulting, two-layer chip that is used for regular MS analysis of protein mixtures.

EXAMPLE 5

Layering a Polycationic Synthetic Polymer Over a Polyanionic Surface

A WCX chip, a polycarboxylic anionic surface, is layered with polyethyleneimine to thus obtain a cationic surface. To this end a 5% aqueous solution of polyethyleneimine is first prepared. Once the solution is perfectly clear and filtered, it is layered on the surface of chip spots. The volume of the deposit can vary from 0.5 to 5μ liters. The water is then evaporated and the chip surface extensively washed with water and dried. The polyaminated polymer is attached by ion exchange by a multipoint interaction mode. The cationic chip then is used classically to make MS analysis of protein mixtures.

The present invention provides novel biochip and methods for using them. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

What we claim is:

1. A biochip comprising:
   (a) substrate comprising a covalently coupled coating that has ionic groups; and
   (b) polymer coating comprising
   (1) ionic groups of a charge opposite to the coating, whereby the polymer coating is ionically bound to the substrate coating, and
   (2) binding groups,
   wherein the biochip is adapted to engage a probe interface of a mass spectrometer and wherein the polymer coating comprises apolysaccharide, a polysaccharide derivative, or dextran.

2. The biochip according to claim 1, wherein the substrate coating comprises anionic groups and the polymer coating comprises cationic groups.

3. The biochip according to claim 1, wherein the polymer coating comprises DEAE dextran.

4. The biochip according to claim 2, wherein the polymer coating comprises cationic groups and hydrophobic groups.

5. The biochip according to claim 4, wherein the hydrophobic group is selected from an aliphatic, aromatic or heterocyclic group.

6. The biochip according to claim 2, wherein the polymer coating is attached to the substrate coating via ion exchange by a multipoint interaction mode.

7. The biochip according to claim 1, wherein the substrate coating comprises cationic groups and the polymer coating comprises anionic groups.

8. The biochip according to claim 1, wherein the polymer coating comprises a carboxymethyl dextran polymer.

9. The biochip according to claim 7, wherein the polymer coating comprises an alginic acid polymer or a polyacrylic acid.

10. The biochip according to claim 7, wherein the polymer coating comprises anionic groups and hydrophobic groups.

11. The biochip according to claim 10, wherein the hydrophobic group is selected from an aliphatic, aromatic or heterocyclic group.

12. The biochip according to claim 7, wherein the polymer coating is attached to the substrate coating via ion exchange by a multipoint interaction mode.

13. The biochip according to claim 1, wherein the polymer coating comprises linear or branched soluble polymers.

14. The biochip according to claim 1, wherein the functionality of the binding groups is other than that of the ionic groups of the polymer coating.

15. The biochip according to claim 1, wherein the polymer coating further comprises energy absorbing moieties.

16. The biochip according to claim 1, wherein the polymer coating comprises a a polysaccharide.

17. The biochip according to claim 1, wherein the polymer coating comprises a polysaccharide derivative.

18. The biochip according to claim 17, wherein the synthetic ionic coating polymer is hydrophilic or hydrophobic.

19. The biochip according to claim 1, wherein the substrate comprises a material selected from metal and synthetic polymer.

20. The biochip according to claim 1, wherein the binding group of the polymer coating is a functionality selected from an anionic functionality, a cationic functionality, a metal chelate functionality, a hydrophbobic functionality, a hydrophilic functionality, a dye functionality or a biospecific functionality.

21. A method comprising:
    (a) providing a biochip of claim 1;
    (b) depositing an analyte on the polymer coating so that the analyte binds to the binding group;
    (c) desorbing/ionizing the analyte from the biochip with photo-irradiation; and
    (d) detecting the desorbed/ionized analyte.

22. The method of claim 21 further comprising applying a matrix to the analyte after deposition.

23. The method of claim 22 wherein the photo-irradiation is laser irradiation.

24. The biochip of claim 1 further comprising an analytes bound to the binding groups and a matrix material applied to the surface of the biochip.

25. A kit comprised of:
    (a) biochip comprising a substrate that is adapted to engage a probe interface of a mass spectrometer, wherein the substrate has a covalently coupled coating that has ionic groups; and
    (b) a receptacle containing a linear polymer that comprises
    (1) ionic groups of opposite charge to those on the substrate and
    (2) binding groups,
    wherein the polymer coating comprises a detran polymer.

26. The kit according to claim 25, further comprising instructions for coating the biochip with a coating of the polymer so that the polymer coating ionically binds to the substrate coating.

27. The kit according to claim 25, wherein the biochip has anionic groups and the polymer coating has cationic groups.

28. The kit according to claim 25, wherein the biochip has cationic groups and the polymer coating has anionic groups.

29. The kit according to claim 25, further comprising a cross-linking agent.

30. The kit according to claim 25, wherein the functionality of the binding groups is other than that of the ionic groups of the polymer coating.

31. The kit according to claim 25, wherein the polymer coating further comprises energy absorbing moieties.

32. The kit according to claim 25, wherein the polymer coating comprises a dextran polymer.

33. The kit according to claim 25, wherein the polymer coating comprises a synthetic ionic polymer.

34. The kit according to claim 25, wherein the substrate comprises a material selected from metal and synthetic polymer.

35. The kit according to claim 25, wherein the binding group is a functionality selected from an anionic functionality, a cationic functionality, a metal chelate functionality, a hydrophbobic functionality, a hydrophilic functionality, a dye functionality or a biospecific functionality.

36. The kit according to claim 25, wherein the polymer coating comprises DEAE dextran.

37. The kit according to claim 25, wherein the polymer coating comprises a carboxymethyl dextran polymer.

38. The kit of claim 25 further comprising (c) a receptacle containing a matrix material for laser desorption/ionization mass spectrometry.

39. A method of making a biochip comprising:
    (a) providing a substrate comprising a coating layer of ionic material bound to the substrate; and
    (b) contacting the substrate with a linear polymer comprising ionic groups of a charge opposite to those of the ionic material, whereby the linear polymer attaches to the substrate through ionic bonds
wherein the linear polymer comprises a dextran polymer.

40. The method according to claim 39, wherein the biochip has anionic groups and the polymer coating has cationic groups.

41. The method according to claim 39, wherein the biochip has cationic groups and the polymer coating has anionic groups.

42. The method according to claim 39, wherein the linear polymer comprises binding groups for a analyte.

43. The method according to claim 42, wherein the functionality of the binding groups is other than that of the ionic groups of the polymer coating.

44. The method according to claim 39, wherein the linear polymer comprises energy absorbing moieties.

45. The method according to claim 39, wherein the liner polymer comprises a dextran polymer.

46. The method according to claim 39, wherein the liner polymer comprises a synthetic ionic polymer.

47. The method according to claim 39, wherein the substrate comprises a material selected from metal and synthetic polymer.

48. The method according to claim 39, wherein the polymer coating comprises DEAE dextran.

49. The method according to claim 39, wherein the polymer coating comprises a carboxymethyl dextran polymer.

50. A biochip comprising:
    (a) substrate comprising a covalently coupled coating that has ionic groups; and
    (b) polymer coating comprising
       (1) ionic groups of a charge opposite to the coating, whereby the polymer coating is ionically bound to the substrate coating, and
       (2) EAM functionalities,
wherein the biochip is adapted to engage a probe interface of a mass spectrometer and wherein the polymer comprises a dextran polymer.

51. The biochip of claim 50 wherein the polymer coating further comprises binding groups.

52. A method comprising:
    (a) providing a biochip of claim 50;
    (b) depositing an analyte on the polymer coating;
    (c) desorbing/ionizing the analyte from the biochip with photo-irradiation; and
    (d) detecting the desorbed/ionized analyte.

53. The method of claim 52 wherein the photo-irradiation is laser irradiation.

54. A kit comprised of:
    (a) biochip comprising a substrate that is adapted to engage a probe interface of a mass spectrometer, wherein the substrate has a covalently coupled coating that has ionic groups; and
    (b) a receptacle containing a linear polymer that comprises
       (1) ionic groups of opposite charge to those on the substrate and
       (2) EAM functionalities,
wherein the linear polymer comprises a dextran polymer.

* * * * *